United States Patent [19]
Subbiah

[11] Patent Number: 5,945,546
[45] Date of Patent: Aug. 31, 1999

[54] PURIFICATION OF SCLAREOLIDE

[76] Inventor: Ven Subbiah, R. J. Reynolds Tobacco Company Avoca Division P.O. Box 129, Avoca Rd., Merry Hill, N.C. 27957

[21] Appl. No.: 08/824,147

[22] Filed: Mar. 25, 1997

[51] Int. Cl.$^6$ .............................. C07D 307/92; C12P 17/04
[52] U.S. Cl. ............................................ 549/299; 435/126
[58] Field of Search ............................ 549/299; 435/126

[56] References Cited

U.S. PATENT DOCUMENTS

| | | | |
|---|---|---|---|
| 3,060,172 | 10/1962 | Teague, Jr. et al. | 260/236.6 |
| 3,096,346 | 7/1963 | Giles et al. | 549/299 |
| 4,970,163 | 11/1990 | Farbood et al. | 435/255 |
| 5,155,029 | 10/1992 | Farbood et al. | 435/125 |
| 5,212,078 | 5/1993 | Farbood et al. | 435/126 |
| 5,247,100 | 9/1993 | Gerke et al. | 549/299 |
| 5,525,728 | 6/1996 | Schneider et al. | 549/299 |

OTHER PUBLICATIONS

Ruzicka et. al., "Höhere Terpenverbindungen" etc., Helvetica Chim. Acta, vol. 14, pp. 645–650, 1931.

Sharma et al.; "E.1. A Review on Clary Sage (*Salvia Sclarea* L.)"; *CROMAP*, 7(1):39–48 (1985).

*Primary Examiner*—Bernard Dentz
*Attorney, Agent, or Firm*—Myers Bigel Sibley & Sajovec

[57] ABSTRACT

A method for purifying sclareolide comprises a separation step wherein debris, e.g., microbial cell debris is removed, and further comprises extracting an organic solution of sclareolide with an acid solution, followed by an extraction of the partially purified sclareolide with a basic solution, thus yielding sclareolide of very high purity.

20 Claims, No Drawings

PURIFICATION OF SCLAREOLIDE

The present invention relates to methods for purifying sclareolide from crude sclareolide preparations.

BACKGROUND OF THE INVENTION

Clary sage is cultivated mainly for the production of its essential oil, sclareol, and sclareol derivatives. U.S. Pat. No. 3,060,172 describes a process for the isolation of sclareol from clary sage. One sclareol derivative, sclareolide, has been used extensively as a major perfume component, as a wine and foodstuffs flavorant, and as a cigarette flavorant. It has therefore been of interest to develop methods of producing high-purity sclareolide in large amounts.

U.S. Pat. Nos. 5,525,728 to Schneider et al., and 5,247,100 to Gerke et al. describe processes for the production of sclareolide from sclareol. Briefly, these processes use a ruthenium catalyst and an oxidation step to convert sclareol into a crude sclareolide product. Sclareolide may be also be produced by the methods generally described in U.S. Pat. Nos. 4,970,163 and 5,212,078, both to Farbood et al. Generally, the Farbood et al. methods utilize a biotransformation (fermentation) process in which one or more microorganisms (e.g., *Cryptococcus albidus, Bensigntonia ciliata*) are used to convert sclareol into useful sclareolide compounds. Although the microbial transformation procedure is preferable to the chemical conversion process, the sclareolide product that is provided by biotransformation contains microbial cell debris and other fermentation by-products that render the sclareolide unsuitably impure. Accordingly, an additional purification process is required in order to provide a sclareolide product that is suitable for commercial purposes. The existing processes that are used to further purify sclareolide produced by biotransformation are inefficient in removing microbial cell debris, and generally involve a costly recrystallization step in which a significant amount of sclareolide is lost in the mother liquor.

Accordingly, it is highly desirable to provide an alternative method of purifying sclareolide that has been produced by biotransformation. Such a method would desirably eliminate cell debris and other fermentation by-products from the sclareolide product, and provide sclareolide with very high purity levels and enhanced aroma and appearance characteristics.

SUMMARY OF THE INVENTION

The present invention relates to a method of purifying sclareolide, and particularly sclareolide that has been prepared by a biotransformation process, by using an acid/base extraction method that includes a filtration step. In this method, crude sclareolide is first provided in an organic solution. The organic solution is then separated by, e.g., filtration to remove debris, such as microbial cell debris. The separated organic solution is extracted by an acidic solution to provide an organic phase containing partially purified sclareolide, which organic phase is then extracted with a basic solution to provide an organic phase containing purified sclareolide. The sclareolide is then collected from the organic phase in its purified form.

The present invention provides advantages over existing methods of purifying sclareolide produced by, e.g, biotransformation of sclareol in that it is effective in decreasing the amount of cell debris and other fermentation by-products from the sclareolide product, and provides sclareolide with very high purity levels.

DETAILED DESCRIPTION OF THE INVENTION

The present invention can be used to purify sclareolide that has been produced by any method known in the art. Exemplary methods of producing sclareolide include the chemical oxidation methods provided in U.S. Pat. Nos. 5,525,728 to Schneider et al. and 5,247,100 to Gerke et al., and the biotransformation/fermentation methods described in U.S. Pat. Nos. 4,970,163 and 5,212,078 to Farbood et al., the disclosures of which patents are incorporated herein by reference in their entirety. Sclareolide produced by these methods is normally provided in wet or dry cake form, and is generally from about 90% to 95% pure.

In the method of the present invention, sclareolide that is to be purified is first provided as an organic solution of sclareolide. This organic solution may optionally be extracted with a liquid having an aqueous character (e.g., water) in order to provide an organic fraction containing sclareolide. The organic solution of sclareolide, or organic fraction containing sclareolide, is then separated in order to remove unwanted debris, e.g., microbial cell debris and other fermentation by-products, thus providing an organic fraction containing sclareolide that has a reduced debris content, and is preferably essentially free of debris. This separated organic fraction is then extracted with an acidic solution comprising an acidic liquid having an aqueous character. After extraction with the acidic solution, the remaining organic fraction containing sclareolide may optionally be washed with a liquid having an aqueous character. The organic fraction containing sclareolide that remains after the acid extraction step or after the optional washing step may further and optionally be subjected to an oxidizing extraction in order to oxidize any sclareol that may remain after, e.g., a fermentation process for microbially transforming sclareol to sclareolide. After any or all of the acid-extraction, washing, and oxidizing steps, the organic fraction containing sclareolide is then extracted with a basic solution comprising an basic liquid having an aqueous character. After extraction with the basic solution, the remaining organic fraction containing sclareolide may optionally be washed with a liquid having an aqueous character (e.g., water). After the extraction and washing steps, the organic solvent is removed from the organic fraction containing sclareolide to yield purified sclareolide. The purified sclareolide can then be collected and further dried or concentrated if desired.

Organic solutions of sclareolide may be provided by dissolving sclareolide in an appropriate organic solvent. Suitable organic solvents include hexane, ethyl acetate, petroleum ether, and ethyl ether, with hexane being particularly preferred. In an organic sclareolide solution, the solution preferably contains not less than 15% of sclareolide by weight, preferably no less than 20% by weight, and most preferably no less than 25% by weight.

The organic solution of sclareolide may optionally be washed or extracted with liquid having an aqueous character to provide an organic phase containing the sclareolide. The terms "liquid having an aqueous character" or "aqueous liquid," as used herein, is a liquid which consists primarily of water, normally greater than about 90 percent water, and can be essentially pure water in certain circumstances. For example, a solvent having an aqueous character can be distilled water, tap water or the like. However, a solvent having an aqueous character can include water having substances such as pH buffers, pH adjusters, organic and inorganic salts, or surfactants incorporated therein. The solvent can also be a cosolvent mixture of water and minor amounts of one or more other solvents (e.g., methanol, ethanol) which are miscible therewith.

The organic solution of sclareolide, or organic phase containing sclareolide, is separated in order to remove debris (i.e., undesired particulate matter) from the organic solution or organic phase. If the starting material sclareolide has been produced by a biotransformation/fermentation method, the separation step desirably removes microbial debris (e.g., yeast cells) and other fermentation by-products such as insoluble fermentation media components and other solid materials. Microbial debris and other fermentation by-products are removed from the organic fraction by any appropriate filtration or separation technique which will be readily apparent to one skilled in the art of fermentation. In a preferred embodiment, microbial debris and other fermentation by-products are removed by crossflow filtration, which filtration comprises passing the organic phase containing sclareolide through a filter with a pore size of not more than 5 $\mu$m, and preferably not more than 1 $\mu$m. The organic phase containing sclareolide is preferably pumped through the filter with pressure of at least 25 pounds/ft$^2$, more preferably with pressure of at least 30 pounds/ft$^2$, and most preferably with pressure of at least 35 pounds/ft$^2$. Suitable filters are commercially available and may comprise, for example, nylon, polyester, glass fiber, polypropylene, or cellulose. The filters may be provided as bag filters or as cartridge filters, as desired by the skilled artisan. Suitable cartridge filters may be obtained from, e.g., the Keystone Filter Division of the MET-PRO Corporation (Hatfield, Pa.). Suitable bag filters are available from, e.g., the Knight Corporation (Ardmore, Pa.). In a preferred embodiment of the present invention, the organic phase containing sclareolide is passed through at least one filter, preferably at least two filters, and most preferably at least three filters. For example, the organic phase may first be passed through a bag filter with a 5 $\mu$m pore size, then through a bag filter with a 1 $\mu$m pore size, and finally through a cartridge filter with a 1 $\mu$m pore size. If filters with differing pore size are used serially as described herein, it is preferred that the organic phase containing sclareolide be passed through the filter with a larger pore size first, and then through the filter or filters with the smaller pore size. The separation step is thus utilized in the present invention to provide an organic fraction containing sclareolide that has a reduced content of microbial debris and other fermentation by-products, and preferably is essentially free of microbial debris and other fermentation by-products.

After the separation step, the organic fraction containing sclareolide is extracted with an acidic solution. An acidic solution as used in the present invention will generally comprise a liquid having an aqueous character, and with a pH of generally no greater than 3.5, preferably no greater than 3.0, and most preferably no greater than 2.5. The aqueous liquid may be made acidic by combining the liquid with an appropriate amount of a suitable acid, such as sulfuric acid, hydrochloric acid, or tartaric acid, with sulfuric acid being preferred. The acidic solution is used to extract the filtered, essentially debris-free organic fraction containing sclareolide. In one embodiment of the invention, the acidic solution is mixed with the organic phase containing sclareolide in a proportion of about 1:1 of acid solution to organic solution, and preferably in a proportion of about 0.5:1 of acid solution to organic solution. The acid solution and organic solution are preferably mixed under stirring or agitation conditions. The organic and aqueous phases are allowed to separate after being mixed together. The organic phase will include the desired sclareolide, while the aqueous phase will contain impurities, especially amine impurities. The aqueous phase is then removed, leaving an organic phase containing partially purified sclareolide. The acidic extraction is performed at least once, but may be repeated if desired or deemed appropriate by the skilled artisan.

After being extracted with the acidic solution, the organic fraction containing purified sclareolide may optionally be washed or extracted at least once with an aqueous liquid (e.g., water) as described above.

After either the acid extraction step or the optional washing step, the organic phase containing sclareolide may further and optionally be extracted with an oxidizing solution in order to remove any sclareol that remains after, for example, the biotransformation of sclareol to sclareolide. An oxidizing solution within the scope of the present invention will generally comprise an oxidant in solution with a liquid having an aqueous character. Such an oxidizing solution may be prepared by combining an aqueous liquid with the appropriate oxidant. Suitable oxidants within the scope of the present invention include, but are not limited to, sodium permanganate (NaMnO$_4$) and potassium permanganate (KMnO$_4$), with KMnO$_4$ being preferred. KMnO$_4$ is useful in oxidizing olefins, primary alcohols and aldehydes to carboxylic acids, which may then be removed in the subsequent basic extraction step. The skilled artisan will thus appreciate that while sclareol is oxidized by KMnO4$_1$, sclareolide is stable in the presence of KMnO$_4$. However, any oxidant in which sclareolide is stable but which oxidizes sclareol is contemplated as being within the scope of the invention. The oxidizing solution will preferably comprise at least 0.2% oxidant by weight, more preferably at least 0.3% oxidant by weight, and most preferably at least 0.4% oxidant by weight. In a preferred embodiment of the invention, the oxidizing solution extraction is performed by combining and mixing the oxidizing solution with the organic phase containing sclareolide. The oxidizing solution may be combined with the organic phase containing sclareolide in a proportion of about 1:1 (by volume) of oxidizing solution to organic phase, and preferably in a proportion of about 0.5:1 of oxidizing solution to organic phase. The oxidizing solution and the organic phase are preferably mixed under stirring or agitation conditions. The organic and aqueous phases are allowed to separate after being mixed together. The aqueous phase is then removed, leaving an organic phase containing partially purified sclareolide. The organic phase containing sclareolide will contain less sclareol after the oxidizing extraction than did the organic phase containing sclareolide prior to the oxidizing extraction step. The oxidizing extraction is performed at least once, but may be repeated if desired or deemed appropriate by the skilled artisan.

After being extracted with the oxidizing solution, the organic fraction containing partially purified sclareolide may optionally be washed or extracted at least once with an aqueous liquid as described above.

After the acid extraction step, or after the optional oxidizing extraction step, or after either of the optional washing steps that may be performed after the acid extraction step or the oxidizing extraction step, the remaining organic phase containing partially purified sclareolide is extracted with a basic solution. A basic solution as used in the present invention may be a carbonate solution, such as a potassium carbonate solution or sodium carbonate solution, but may also be a potassium hydroxide solution or a sodium hydroxide solution, with the potassium hydroxide solution being currently preferred. Such a basic solution may be prepared by combining an aqueous liquid with the appropriate base. In one embodiment of the invention, the basic solution will preferably comprise at least 1 percent base by weight, more preferably at least 2 percent base by weight, and most preferably at least 5 percent base by weight. In one embodiment of the invention, the basic solution is mixed with the organic phase containing partially purified sclareolide in a proportion of about 1:1 of basic solution to organic phase, and preferably in a proportion of about 0.5:1 of basic solution to organic phase. The basic solution is preferably mixed with the organic phase under stirring or agitation conditions. After mixing, the organic and aqueous phases are allowed to separate. The organic phase will comprise purified sclareolide, while the aqueous phase will contain impurities, especially phenol and acidic impurities. The aqueous phase is then removed, leaving an organic phase containing purified sclareolide. The basic extraction is performed at least once, but may be repeated if desired or deemed appropriate by the skilled artisan.

After being extracted with the basic solution, the organic fraction containing purified sclareolide may optionally be washed or extracted at least once with an aqueous liquid as described above. After the extraction and washing steps have been completed, the organic solvent may be removed from the sclareolide by any method that will be apparent to one skilled in the art, including, e.g., distillation, evaporation, and the like. If desired, an additional purification step comprising, e.g., recrystallization may be performed. The remaining purified sclareolide may be dried using any drying method or apparatus known to one skilled in the art, including, e.g., a concentrator, flaker, or vacuum stripper.

The method of the present invention may be carried out at room temperature. In an alternative embodiment of the invention, the purification method of the present invention is carried out a temperature of greater than 100° F. (380° C.), preferably at a temperature of at least 130° F. (54° C.), and most preferably to a temperature of at least 140° F. (60° C.).

The resulting purified sclareolide product is typically at least about 95% pure (i.e., the sclareolide product typically comprises at least about 95 sclareolide by weight), and preferably will be at least about 97% pure, and most preferably will be at least about 98% pure, as determined by, e.g., gas chromatography (GC) or gas chromatography-mass spectrometry (GC-MS).

The sclareolide purified by any embodiment of the present invention is useful as a fragrance in perfumery, or as a flavoring in foods and beverages, or as a flavorant in tobacco products such as cigarettes.

The following examples are provided in order to further illustrate various embodiments of the invention and are not to be construed as limiting the scope thereof. In the following examples, lbs. means pounds, μm means micrometers, L means liters, ° F. means temperature in degrees Fahrenheit, ° C. means and dH$_2$O means deionized water.

EXAMPLE 1

Analytic Scale Purification of Sclareolide 1 lb. of sclareolide produced by the method of Farbood, et al., supra, was dissolved in 2 L of hexane by stirring. The solution was passed through a nylon filter with a 1 μm pore size to remove yeast cell debris. The filtered solution was extracted twice with 1 L of acidic water (pH 2.5) by stirring. The hexane fraction was separated and extracted twice with 1 L 5% potassium hydroxide by stirring. The upper hexane layer was separated and dried in a concentrator to obtain sclareolide crystals.

The sclareolide crystals were quantitatively analyzed by gas chromatography, and compared in terms of percentage purity with the original starting product. The results of this analysis are presented below in Table 1.

TABLE 1

Quantitative GC Analysis of Unpurified and Purified Sclareolide

| Batch Number | Percentage Purity Unpurified Sclareolide | Percentage Purity Purified Sclareolide |
|---|---|---|
| 1 | 93.1 | 97.5 |
| 2 | 89.7 | 95.1 |
| 3 | 97.2 | 99.6 |

The sclareolide crystals were compared to recrystallized sclareolide that had been purified by known methods, and were found to be comparable in terms of both color and odor.

EXAMPLE 2

Industrial Scale Purification of Sclareolide

700–800 lbs of wet cake sclareolide is dissolved in 1440 gallons of hexane, and heated by steam heating to a temperature of 130° F. (54° C.). After turning the steam off, the temperature of the solution is allowed to drift to 140OF (60OC), and is held at that temperature for one hour. 500 gallons of H$_2$0 that has been heated to a temperature of 140OF (60OC) is added to the sclareolide/hexane solution, agitated with the hexane solution, and allowed to separate overnight. The water layer is drained away, and the hexane layer containing sclareolide collected.

An acidic water solution is prepared by mixing 700 gallons of water with 3 gallons of 7N H$_2$SO4$_1$ The acidic water solution is heated to 140OF (60OC). The hexane solution containing sclareolide is pumped under 35 lbs/ft$^2$ pressure through a first polypropylene bag filter (Model No. P5P2, Knight Corporation (Ardmore, PA), 5 AM pore size and 32 inches long); then through a second polypropylene bag filter (Model No. PlP2, Knight Corporation, 1 AM pore size, 32 inches long); then through a polypropylene cartridge filter (Model No. 08FP01030D, Keystone Filter Division (Ardmore, PA), 1 Am pore size, 30 inches long); and finally into the container containing the heated acidic water. After the entire filtered hexane solution is added to the acidic water, the combination is agitated for three minutes and allowed to separate for one hour. The acid wash is then drained away.

A basic solution is prepared by adding 250 lbs. of potassium hydroxide to 600 gallons H$_2$0, and heating the solution to 140OF (60OC). The carbonate wash is added to the sclareolide solution, agitated for three minutes, and allowed to separate for 1 hour. The carbonate wash is then drained away, leaving a hexane fraction containing sclareolide.

The remaining hexane fraction is washed with water by adding 500 gallons of H$_2$0 heated to 140OF (60OC) to the hexane fraction, agitating for three minutes, and allowing the phases to separate for 1 hour. The water phase is removed, leaving the sclareolide in the hexane fraction. The hexane is then distilled away from the purified sclareolide product by heating the hexane fraction to a temperature of about 250° F. (121° C.) and removing the vapor phase. The purified sclareolide remaining is then processed through a flaker.

In the specification and examples, there have been disclosed preferred embodiments of the invention. Although specific terms are employed in these examples, they are used in a generic and descriptive sense only and not for the purpose of limitation, the scope of the invention being defined by the following claims.

That which is claimed is:

1. A process for purifying sclareolide, comprising the steps of:
   (a) providing an organic sclareolide solution;
   (b) separating the organic sclareolide solution of step (a) to provide an organic phase containing sclareolide with a reduced amount of debris;
   (c) extracting the organic phase containing sclareolide of step (b) with an acidic aqueous solution to provide an organic phase containing partially purified sclareolide;
   (d) extracting the organic phase containing partially purified sclareolide of step (c) with a basic aqueous solution to provide an organic phase containing purified sclareolide; and
   (e) collecting the purified sclareolide produced by step (d).

2. The process according to claim 1, wherein said organic sclareolide solution of step (a) comprises sclareolide produced by the microbial transformation of sclareol.

3. The process according to claim 1, wherein the organic sclareolide solution of step (a) is produced by dissolving sclareolide in an organic solvent.

4. The process according to claim 3, wherein said organic solvent is hexane.

5. The process according to claim 1, whereby said separating step (b) comprises filtration.

6. The process according to claim 2, whereby said separating step (b) provides an organic phase containing sclareolide with a reduced amount of microbial debris.

7. The process according to claim 2, whereby said separating step (b) provides an organic phase containing sclareolide essentially free of microbial debris.

8. The process according to claim 1, wherein the acidic solution of step (c) is water having a pH of less than about 3.0.

9. The process according to claim 1, wherein the basic solution of extracting step (d) is an aqueous solution of potassium hydroxide.

10. The process according to claim 1, whereby steps (a) through (d) are carried out at a temperature of between about 130 to 140° F. (54 to 60° C.).

11. The process according to claim 1, further comprising the step of extracting the organic sclareolide solution of step (a) with an aqueous liquid prior to separating step (b).

12. The process according to claim 11, wherein said aqueous liquid is water.

13. The process according to claim 1, further comprising the step of washing the organic phase produced by extracting step (c) with an aqueous liquid prior to extracting step (d).

14. The process according to claim 13, wherein said aqueous liquid is water.

15. The process according to claim 1, further comprising the step of contacting the organic phase produced by extraction step (c) with an oxidizing solution prior to extraction step (d) to remove the organic solution.

16. The process according to claim 15, wherein said oxidizing solution is a solution of potassium permanganate.

17. The process according to claim 1, further comprising the step of washing the organic phase produced by step (d) with an aqueous liquid prior to collection step (e).

18. The process according to claim 1, whereby the collection step (e) is carried out by distillation.

19. The process according to claim 1, wherein said purified sclareolide of step (e) has a purity of more than 95%.

20. The process according to claim 1, further comprising the step of drying the purified sclareolide after said collecting step (e).

* * * * *

UNITED STATES PATENT AND TRADEMARK OFFICE
CERTIFICATE OF CORRECTION

PATENT NO. : 5,945,546
DATED : August 31, 1999
INVENTOR(S) : Ven Subbiah

It is certified that error appears in the above-identified patent and that said Letters Patent is hereby corrected as shown below:

On the title page item
[76] Inventor:,

"Ven Subbiah, R. J. Reynolds Tobacco Company Avoca Division P.O. Box 129, Avoca Rd., Merry Hill, N.C. 27957"

Should read

--Ven Subbiah, Edenton, N.C.--

Signed and Sealed this

Twenty-fourth Day of April, 2001

Attest:

NICHOLAS P. GODICI

*Attesting Officer*  *Acting Director of the United States Patent and Trademark Office*